United States Patent [19]
Heinrich et al.

[11] Patent Number: 5,733,847
[45] Date of Patent: Mar. 31, 1998

[54] SELECTIVE HERBICIDAL COMPOSITIONS IN THE FORM OF CONCENTRATED MICROEMULSIONS

[75] Inventors: Rudolf Heinrich, Kelkheim; Detlev Haase, Sulzbach am Taunus; Thomas Maier, Frankfurt am Main, all of Germany

[73] Assignee: Hoechst Aktiengesellschaft, Frankfurt, Germany

[21] Appl. No.: 450,810

[22] Filed: May 25, 1995

Related U.S. Application Data

[63] Continuation of Ser. No. 259,555, Jun. 14, 1994, abandoned, which is a continuation of Ser. No. 943,502, Sep. 11, 1992, abandoned.

[30] Foreign Application Priority Data

Sep. 14, 1991 [DE] Germany .................... 41 30 707.0
Oct. 29, 1991 [DE] Germany .................... 41 35 587.3

[51] Int. Cl.$^6$ .................... A01N 25/02; A01N 25/30; A01N 25/32
[52] U.S. Cl. .................... 504/116; 504/106; 504/270; 504/125
[58] Field of Search .................... 504/106, 116, 504/270, 125; 71/DIG. 1

[56] References Cited

U.S. PATENT DOCUMENTS

| | | | |
|---|---|---|---|
| 4,130,413 | 12/1978 | Handte et al. | 504/270 |
| 4,531,969 | 7/1985 | Nestler et al. | 504/270 |
| 4,639,266 | 1/1987 | Henbach et al. | 548/262 |
| 4,870,103 | 9/1989 | Röechling et al. | 514/521 |
| 4,973,352 | 11/1990 | Heinrich et al. | 71/DIG. 1 |
| 5,074,905 | 12/1991 | Frisch et al. | 504/116 |
| 5,078,782 | 1/1992 | Nielsen et al. | 504/116 |

FOREIGN PATENT DOCUMENTS

| | | |
|---|---|---|
| 1227353 | 9/1987 | Canada . |
| 0118759 | 9/1984 | European Pat. Off. . |
| A-0 118 759 | 9/1984 | European Pat. Off. . |
| A-0 257 286 | 3/1988 | European Pat. Off. . |
| 0174562 | 3/1989 | European Pat. Off. . |
| A-0 330 904 | 9/1989 | European Pat. Off. . |

OTHER PUBLICATIONS

The Pesticide Manual, Northing, editor, British Crop Protection Council, 9th edition, p. 373, 1991.

*Primary Examiner*—S. Mark Claardy
*Attorney, Agent, or Firm*—Frommer Lawrence & Haug LLP

[57] ABSTRACT

The invention relates to novel herbicidal compositions which comprise herbicidal active substances from the class of the phenoxyphenoxy- and heteroaryloxyphenoxy-carboxylic acid derivatives, a dispersant from the class of the fatty alcohol polyoxypropylene-polyoxyethylene ethers and/or the polyoxyethylene-polyoxypropylene block copolymers, emulsifier or wetting agent from the group comprising calcium dodecylbenzenesulfonate, fatty acid polyglycol esters, the ethoxylated nonylphenols and the alkanol polyglycol ethers, organic solvents and water, in the form of microemulsions which have low viscosity and are stable chemically and with regard to their technical properties in use.

The invention furthermore relates to a process for preparing these microemulsions by stirring, shaking or static mixing. Prior to the biological application of these formulations, they are mixed with water and thus give spray mixtures which are perfect with regard to their technical properties in use.

14 Claims, No Drawings

SELECTIVE HERBICIDAL COMPOSITIONS IN THE FORM OF CONCENTRATED MICROEMULSIONS

This application is a continuation of application Ser. No. 08/259,555, filed Jun. 14, 1994, which is a continuation of application Ser. No. 07/943,502, filed Sep. 11, 1992.

The invention relates to novel liquid selective herbicidal compostions which comprise the active substances in the form of microemulsions which have low viscosity and are stable chemically and with regard to their technical properties in use. EP-A-118,759 and Canadian Patent 1,227,353 disclose that solutions of phenoxyphenoxycarboxylic acids and their derivatives in aromatic solvents can be formulated in the aqueous phase with the aid of terminal phosphorylated ethylene oxide/propylene oxide/ethylene oxide block copolymers to give milky-white concentrated emulsions. However, it is possible that the use of substantial amounts of wetting agent and a higher concentration of active substance results in semi-liquid, high viscose macroemulsions which can cause problems during application.

It is furthermore known that herbicidal active substances from the group of the phenoxyphenoxy herbicides and of the benzoxazolyloxyphenoxycarboxylates can be combined with other compounds which have a selectively herbicidal action or with crop-protecting agents (safeners) to give finished formulations which are stable chemically and with regard to their technical properties in use, with the purpose of optimizing the spectrum of action. EP-A-174,562 and U.S. Pat. 4,639,266 describe that herbicidally active benzoxazolyloxyphenoxycarboxylic acid derivatives such as, for example, ethyl 2-[4-(6-chloro-1,3-benzoxazol-2-yloxy)-phenoxy]propionate (fenoxaprop-ethyl) can be combined with safeners from the group of the optionally substituted 1-aryl-3-alkoxy-carbonyl-5-alkyl-1,2,4-triazol compounds in such a way that suitable amounts of a formulation of the 1,2,4-triazol mentioned and of other herbicidal active substances, for example from the group of the growth regulators and other compounds are added to the spray mixture shortly before the fenoxaprop-ethyl is applied, so as to utilize the advantageous biological properties of the combination of these active substances in this manner. However, this method is relatively complicated and time-consuming. This may result in incorrect dosage rates in practice.

It was therefore an object to circumvene these difficulties and to prepare biologically active, homogenous preparations of these active substances which are stable chemically and with regard to their technical properties in use, in the form of environmentally-friendly microemulsions which have low viscosity and which meet the demands in practice.

It was important to realize, in particular, that the different active substance classes can interact with each other adversely in the presence of customary formulation auxiliaries and stabilizers when exposed to increased storage temperatures, which results in a noticeable change from the chemical point of view, in particular in the case of prolonged storage periods, the result being biologically less active, or even inactive, components. The present invention overcomes these shortcomings.

Surprisingly, it has now been found that the use of selective emulsifiers together with the abovementioned active substances allows transparent microemulsions to be prepared which remain stable physically and chemically, even after prolonged storage both at low and at higher temperatures, and which do not show signs of inhomogeneity.

The present invention relates to liquid, selectively herbicidal agents on the basis of environmentally-friendly concentrated microemulsions which comprise, besides a) at least one herbicidal active substance from the class of the phenoxyphenoxy- or heteroaryloxyphenoxycarboxylic acid derivatives, b) optionally at least one compound from the group of the substituted 1-aryl-3-alkoxycarbonyl-5-alkyl-1,2,4-triazoles, the substituted 1-aryl-5-alkoxy-carbonyl-5-alkyl-pyrazoline-3-carboxylates and of the 5-substituted 8-quinolinoxyacetates, c) optionally at least one compound from the class of the substituted aryloxyalkanoic acids and of the halogenated hydroxybenzonitriles, d) at least one dispersant from the class of the fatty alcohol polyoxypropylene-polyoxyethylene ethers and of the polyoxyethylene-polyoxypropylene block copolymers, e) optionally one or more carboxylates and/or phosphates of aliphatic monoalcohols, dialcohols or polyalcohols as stabilizing agent, f) at least one emulsifier or wetting agent from the group comprising calcium dodecylbenzenesulfonate, fatty acid polyglycol esters such as ethoxylated castor oil, the ethoxylated nonylphenols and the alkanol polyglycol ethers, g) one or more organic solvents, preferably selected from the group comprising aromatics, ketones and pyrrolidones, h) optionally at least one cosolvent and/or antifreeze selected from the group comprising polyols such as ethylene glycol, propylene glycol, glycerol, polyglycols and sugar alcohols, sugars and urea, i) optionally at least one dispersant from the series of the cresol-formaldehyde condensation products with an aromatic sulfonic acid, such as ®Dispergiermittel SS (Hoechst AG) and j) water.

Herbicidal phenoxy- or heteraryloxyphenoxycarboxylic acid derivatives which are preferably employed are the substituted phenoxyphenoxy-, quinoxalyloxyphenoxy-, pyridyloxyphenoxy-, benzoxazolyloxyphenoxy- or benzothia-zolyloxyphenoxy/carboxylates in the form of the pure optical isomers or in the form of isomer mixtures (for example racemates). These compounds are known, for example, from DE-A-2,136,828, U.S. Pat. No. 4,238,626, DE-A-2,223,894, U.S. Pat. No. 3,954,442, GB Patent 2,042, 539, GB Patent 1,599,121, DE-A-2,640,730 and U.S. Pat. No. 4,130,413. Particularly suitable are the ($C_1$–$C_4$)alkyl, ($C_2$–$C_4$)alkenyl or ($C_3$–$C_4$)alkynyl esters or their salts.

Substances which must be mentioned in particular amongst these herbicides (Component (a)) are the phenoxyphenoxy and benzyloxyphenoxycarboxylic acid derivatives such as methyl 2-(4-(2,4-dichlorophenoxy)phenoxy)propionate (diclofop-methyl), methyl 2-(4-(4-bromo-2-chlorophenoxy)phenoxy) propionate (DE-A-2,601,548), methyl 2-(4-(4-bromo-2-fluorophenoxy)phenoxy) phenoxy)propionate (U.S. Pat. No. 4,808,750), methyl 2-(4-(2-chloro-4-trifluoromethylphenoxy) phenoxy)propionate (DE-A-2,433,067), methyl 2-(4-(2-fluoro-4-trifluoromethylphenoxy) phenoxy)propionate (U.S. Pat. No. 4,808,750), methyl 2-(4-(2,4-dichlorobenzyl)phenoxy)propionate (see DE-A-2,417,487), ethyl 4-(4-(4-trifluoromethylphenoxy)phenoxy)pent-2-enoate, methyl 2-(4-(4-trifluoromethylphenoxy)phenoxy) propionate (DE-A-2,433,067), "uninuclear" heteroaryloxyphenoxyalkanecarboxylic acid derivatives such as ethyl 2-(4-(3,5-dichloropyridyl-2-oxy)phenoxy) propionate (EP-A-2,925), propargyl 2-(4-(3,5-dichloropyridyl-2-oxy)phenoxy) propionate (EP-A-3,114), methyl 2-(4-(3-chloro-5-trifluoromethyl-2-pyridyloxy) phenoxypropionate (haloxyfop-methyl) and the corresponding 2-ethoxyethyl ester (haloxyfop-2-ethoxyethyl); EP-A-3,890], ethyl 2-(4-(3-chloro-5-trifluoromethyl-2-pyridyloxy) phenoxy)propionate (EP-A-3,890), propargyl 2-(4-(3-chloro-5-fluoro-2-pyridyloxy) phenoxy)propionate (EP-A-191,736), butyl 2-(4-(5-trifluoromethyl-2-pyridyloxy)phenoxy) propionate (fluazifop-butyl), 2-[2-[4-(3,5-dichloro-2-pyridyloxy)phenoxy]propionyl]-1,2-oxazolidine (isoxapyrifop) and "binuclear" heteroaryloxyphenoxyalkanecarboxylic acid derivatives such as methyl and ethyl 2-(4-(6-chloro-2-quinoxalyloxy) phenoxy)propionate (quizalofop-methyl and -ethyl), methyl and ethyl 2-(4-(6-fluoro-2-quinoxalyloxy) phenoxy)propionate (J. Pest. Sci., Vol. 10, 61 (1985)), methyl and 2-isopropylidenaminooxyethyl 2-(4-(6-chloro-2-quinolyloxy)phenoxy)propionate (propaquizafop and esters), ethyl 2-(4-(6-chlorobenzoxazol-2-yloxy)phenoxy) propionate (fenoxaprop-ethyl) and ethyl 2-(4-(6-chlorobenzothiazol-2-yloxy) phenoxypropionate (fenthiaprop-ethyl; DE-A-2,640, 730).

Compounds which are suitable for component (b) of the compositions according to the invention, which is optionally to be used, are the compounds mentioned in EP-A-174,562, preferably the 1-(2,4-dichlorophenyl)-3-($C_1$–$C_4$) alkoxycarbonyl-5-haloalkyl-1,2,4-triazole compounds, in particular the 1-(2,4-dichlorophenyl)-3-ethoxycarbonyl-haloalkyl-1,2,4-triazoles, where the haloalkyl radical is preferably $CCl_3$, $CHCl_2$, $CHF_2CF_2$, in particular 1-(2,4-dichlorophenyl)-3-ethoxycarbonyl-5-trichloromethyl-1,2,4-triazole. Compounds which are furthermore suitable are 1-(haloaryl)-5-(ethoxycarbonyl)-5-alkylpyrazoline-3-carboxylates, such as ethyl 1-(2,4-dichlorophenyl)-5-ethoxycarbonyl-5-methylpyrazoline-3-carboxylate, as well as quinolinoxyalkanecarboxylic acid derivatives, such as the (5-chloro-8-quinolinoxy) acetate.

Substances which are suitable as component (c) which is optionally to be used are salts or fatty acid esters of substituted aryloxyalkanoic acids, preferably substituted phenoxy acetic acid derivatives, such as, for example, 2,4 D-butyl or 2,4 D-octyl compounds, as well as MCPA-butyl or MCPA-octyl, furthermore other substituted phenoxyalkanoic acid derivatives such as mecopropisooctyl or mecoprop-P-isobutyl, MCPB-ethyl or MCPB-isooctyl, as well as bromoxynil octanoate or ioxynil octanoate. The compounds mentioned herein are described in "The Pesticide Manual", 9th Edition.

Examples of suitable dispersants (d) are alkyl ethers of polyoxypropylenepolyoxyethylene block copolymers, in particular simple fatty alcohol polyoxypropylene-polyoxyethylene ethers such as, for example, those of the ($C_3$–$C_7$) alcohols, in particular of n-butanol or of isobutanol, such as HOE S3510, HOE S1816 (both: Hoechst AG) and ®Rewopal (Rewo Chemie).

Particularly interesting as Component (e) which has a stabilizing action are low-molecular-weight esters of carboxylic acids with alcohols, diols or polyols, for example esters of aliphatic ($C_2$–$C_5$)carboxylic acids and linear or branched aliphatic ($C_2$–$C_{12}$)alcohols, ($C_2$–$C_{12}$)diols or ($C_2$–$C_{12}$)polyols. Preferred esters are esters of carboxylic acids such as acetic acid, propionic acid, butyric acid or pentanoic acid, in particular acetic acid, with alcohols such as methanol, ethanol, propanol, isopropanol, n-, t- and 2-butanol, isobutanol, n- or 2- pentanol, isopentanol, n- or 2-hexanol, isohexanol, heptanol, octanol, nonanol, decanol, undecanol and dodecanol, or diols, such as glycol, propanediol, butanediol and hexanediol, or polyols, such as glycerol, pentaerythritol and hexitol.

Preferred esters are, in particular, esters of acetic acid with ($C_2$–$C_6$)alcohols or with diols such as 1,4-butanediol, or with triols such as glycerol.

Suitable as component (f) are commercially available emulsifiers, preferably one or more from the group of the alkylbenzenesulfonates, such as calcium dodecylbenzenesulfonate and fatty acid polyglycol esters such as ethoxylated castor oil. Wetting agents which may be part of the formulation are preferably from the group of the alkylphenol polyglycol ethers and alkanol polyglycol ethers.

The ethoxylated castor oil to be used according to the invention has in particular 20 to 60 EO units (EO=ethylene oxide). Products which can be employed are, for example, ®Emulsogen EL 400 or ®Emulsogen EL 360 (Hoechst AG). The ethoxylated nonylphenols have 2–20 EO. These include, for example, ®Arkopal N 100 (Hoechst AG). Alkanol polyglycol ethers which may be mentioned are preferably ethoxylated ($C_8$–$C_{20}$)alkanols having an EO content of 3 to 20 EO, for example ®Genapol X 060 (Hoechst AG). The fatty acid polyglycol esters have in particular 12–18 carbon atoms in the fatty acid moiety. Of the emulsifiers mentioned, ethoxylated castor oil and the alkanol polyglycol ethers are most suitable according to the invention.

Furthermore, other customary anionic non-ionic emulsifiers or wetting agents such as, for example, sodium alkyl diglycol ether sulfates, can be added in small amounts (up to 10%) to the formulations according to the invention without essentially changing the properties of the formulations. The amount of dispersants from the series of the cresol-formaldehyde condensation products with an aromatic sulfonic acid is up to 10% by weight, preferably up to 5% by weight.

Suitable solvents are all of those which are not miscible with water and which are acceptable for use in agriculture, preferably from the groups of the aromatics, ketones and pyrrolidones.

Examples of aromatic solvents are toluene, xylenes, higher-boiling fractions of aromatics, methylnaphthalenes and solvents from amongst the ®Solvesso series (Esso), suitable ketones are, in particular, cyclohexanone as well as acetophenone, furthermore pyrrolidones, such as N-methylpyrrolidone (NMP), or mixtures of the abovementioned solvents.

The crop-protecting combinations according to the invention have an overall active substance content of from 3–50% by weight, preferably 20–35% by weight; furthermore 5–60% by weight, preferably 10–50% by weight, of solvent or solvent mixture; 10–40% by weight, preferably 15–25% by weight, of emulsifiers and/or wetting agents, 0.1–15% by weight, preferably 1–10% by weight, of cosolvent and/or antifreeze, as well as 5–70% by weight, preferably 15–50% by weight, of water.

The ratio by weight of aqueous to organic phase in the formulations can vary between 5:1 and 1:5.

The invention furthermore relates to the process for the preparation of the compositions according to the invention. To this end, the required amounts of the abovementioned components are brought into a zone of high turbulence, preferably at temperatures of between 10 and 60° C., expediently at room temperature or just above, until the desired homogenous stable transparent microemulsion has formed.

To carry out the process in practice, the aqueous phase is generally prepared first, for example from the solution of the dispersant, the wetting agent and, if appropriate, additional water. Then, the active substance to be emulsified, which is insoluble in water, is preferably dissolved in the organic solvent, and treated with the amounts of emulsifier. On mixing with water, the resulting organic phase is then exposed to shearing forces, as they occur, for example, during stirring, in static mixers, in colloid mills and/or during treatment with a dissolver. The macroemulsion, which is milky at the beginning, eventually undergoes transition into a transparent microemulsion.

If appropriate, dispersing can be effected by a shaking process or in a static mixer and is continued expediently until the preparation is homogenous. The dispersing procedure is expediently carried out at room temperature but can also be effected at low or increased temperatures.

Being microemulsions, the resulting formulations are stable to chemical degradation of the active substances and to phase separation, even when the active substance contents are comparatively high. They therefore have a very good shelf life and are also suitable for storage under climatically adverse conditions, in particular also at higher temperatures of from 30° to 50° C.

Prior to biological use, the formulations are mixed with water, whereupon they give spray mixtures which are perfect with regard to their technical properties in use (the ready-for-use dilution is preferably from 1:200 to 1:400).

The examples which follow are intended to illustrate the present invention in greater detail without imposing any limitation thereto:

EXAMPLE 1

4.3% by weight of fenoxaprop-P-ethyl are dissolved in 35.0% by weight of an aromatics mixture (boiling range 219°–282° C.) with stirring at 20°–30° C. and the mixture is then treated with 1.1% by weight of a 1-aryl-3-alkoxycarbonyl-5-alkyl-1,2,4-triazole (for example 1-(2,4-dichlorophenyl)-3-ethoxycarbonyl-5-trichlorophenyl-1,2,4-triazole). To this mixture there are added 16.6% by weight of nonylphenol 10 EO and 8.0% by weight of a ($C_{12}$–$C_{18}$) fatty acid polyglycol ester 40 EO and 8.0% by weight of a 70% strength solution of calcium dodecyl-benzenesulfonate in butanol. In another stirred vessel, 16.0% by weight of water are stirred with 4.0% by weight of n-butoxy polyoxypropylene-polyoxyethylene ether, 3.0% by weight of an ethoxylated soya oil and 4.0% by weight of glycerol. The organic phase is added to this solution with further stirring, and the mixture is stirred until a transparent microemulsion which has low viscosity is formed.

EXAMPLE 2

8.5% by weight of fenoxaprop-P-ethyl are dissolved in 30.0% by weight of an aromatics mixture (boiling range 219°–282° C.) with stirring at 20°–30° C. and the mixture is then treated with 2.1% by weight of a 1-aryl-3-alkoxycarbonyl-5-alkyl-1,2,4-triazole (for example 1-(2,4-dichlorophenyl)-3-ethoxycarbonyl-5-trichlorophenyl-1,2,4-triazole). To this mixture there are added 20.4% by weight of nonylphenol 10 EO and 6.0% by weight of a ($C_{12}$–$C_{18}$) fatty acid polyglycol ester 40 EO and 6.0% by weight of a 70% strength solution of calcium dodecyl-benzenesulfonate in butanol. In another stirred vessel, 16.0% by weight of water are stirred with 4.0% by weight of n-butoxy polyoxypropylene-polyoxyethylene ether, 3.0% by weight of an ethoxylated soya oil and 4.0% by weight of glycerol. The organic phase is added to this solution with further stirring, and the mixture is stirred until a transparent microemulsion which has low viscosity is formed.

EXAMPLE 3

8.16% by weight of fenoxaprop-P-ethyl are dissolved in 35.75% by weight of an aromatics mixture (boiling range 219°–282° C.) and 5.0% by weight of NMP with stirring at 20°–30° C. To this mixture there are added 4.08% by weight of a 1-aryl-5-alkoxycarbonyl-5-alkylpyrazoline-3-carboxylate (for example ethyl 1-(2,4-dichlorophenyl)-5-ethoxycarbonyl-5-methylpyrazoline-3-carboxylate) as well as 12.01% by weight of nonylphenol 10 EO and 6.0% by weight of a ($C_{12}$–$C_{18}$) fatty acid polyglycol ester 40 EO. 12.0% by weight of a 70% strength solution of calcium dodecylbenzenesulfonate in butanol are added to the clear solution. In another stirred vessel, 13.0% by weight of water are stirred with 2.0% by weight of n-butoxy polyoxypropylene-polyoxyethylene ether and 2.0% by weight of glycerol. The organic phase is added to this solution with further stirring, and the mixture is stirred until a transparent microemulsion which has low viscosity is formed.

EXAMPLE 4

6.13% by weight of fenoxaprop-P-ethyl are dissolved in 43.63% by weight of an aromatics mixture (boiling range 219°–282° C.) and 3.0% by weight of NMP with stirring at 20°–30° C. To this mixture there are added 3.1% by weight of a 1-aryl-5-alkoxycarbonyl-5-alkylpyrazoline-3-carboxylate (for example ethyl 1-(2,4-dichlorophenyl)-5-ethoxycarbonyl-5-methylpyrazoline-3-carboxylate) as well as 9.14% by weight of nonylphenol 10 EO and 7.0% by weight of a ($C_{12}$–$C_{18}$) fatty acid polyglycol ester 40 EO. 11.0% by weight of a 70% strength solution of calcium dodecylbenzenesulfonate in butanol are added to the clear solution. In another stirred vessel, 13.0% by weight of water are stirred with 2.0% by weight of n-butoxy polyoxypropylene-polyoxyethylene ether and 2.0% by weight of glycerol. The organic phase is added to this solution with further stirring, and the mixture is stirred until a transparent microemulsion which has low viscosity is formed.

EXAMPLE 5

6.13% by weight of fenoxaprop-P-ethyl are dissolved in 44.63% by weight of an aromatics mixture (boiling range 219°–282° C.) and 3.0% by weight of NMP with stirring at 20°–30° C. To this mixture there are added 3.1% by weight of a 1-aryl-5-alkoxycarbonyl-5-alkylpyrazoline-3-carboxylate (for example ethyl 1-(2,4-dichlorophenyl)-5-ethoxycarbonyl-5-methylpyrazoline-3-carboxylate) as well as 9.14% by weight of nonylphenol 10 EO and 7.0% by weight of a ($C_{12}$–$C_{18}$) fatty acid polyglycol ester 40 EO.

8.0% by weight of a 70% strength solution of calcium dodecylbenzenesulfonate in butanol are added to the clear solution. In another stirred vessel, 14.0% by weight of water are stirred with 2.0% by weight of n-butoxy polyoxypropylene-polyoxyethylene ether and 3.0% by weight of glycerol. The organic phase is added to this solution with further stirring, and the mixture is stirred until a transparent microemulsion which has low viscosity is formed.

We claim:

1. A microemulsion comprising:
   at least one herbicidal active substance from the class of the phenoxyphenoxy- and heteroaryloxy-phenoxycarboxylic acid derivatives,
   at least one dispersant from the class of the fatty alcohol polyoxpropylene-polyoxyethylene ethers and of the polyoxypropylene block copolymers,
   at least one emulsifier or wetting agent from the group consisting of calcium dodecylbenzenesulfonate, fatty acid polyglycol esters the ethoxylated nonylphenols and the alkanol polyglycol ethers, one or more organic solvents, and water.

2. A microemulsion as claimed in claim 1, additionally comprising at least one compound selected from the group of the 1-aryl-3-alkoxycarbonyl-5-alkyl-1,2,4-triazoles, 1-aryl-5-alkoxycarbonylpyrazoline-3-carboxylates and 5-substituted 8-quinolinoxy-acetates.

3. A microemulsion as claim 1, additionally comprising at least one compound from the class of the substituted aryloxyalkanoic acids and/or halogenated hydroxybenzonitriles.

4. A microemulsion as claimed in claim 1, additionally comprising one or more carboxylates and/or phosphates of aliphatic monoalcohols, dialcohols or polyalcohols as stabilizing agent.

5. A microemulsion as claimed in claim 1, additionally comprising at least one cosolvent and/or antifreeze selected from the group consisting of polyols, sugars and urea.

6. A microemulsion as claimed in claim 1, additionally comprising at least one dispersant from the series of the cresol-formaldehyde condensation products with an aromatic sulfonic acid.

7. A microemulsion as claimed in claim 1, comprising 3–50% by weight of active substance; 5–60% by weight of solvent or solvent mixture; 10–40% by weight of emulsifier and/or wetting agent; 0.1–15% by weight of cosolvent and/or antifreeze, as well as 5–70% by weight of water.

8. A microemulsion as claimed in claim 1, comprising fenoxaprop-ethyl in the D-form or as a stereoisomer mixture.

9. A microemulsion as claimed in claim 1, comprising at least one compound from the series
   1-(2,4-dichlorophenyl)-3-ethoxycarbonyl-5-trichloromethyl-1,2,4-triazole,
   1-(2,4-dichlorophenyl)-5-ethoxycarbonyl-5-methylpyrazoline-3-carboxylate and
   (5-chloro-8-quinolinoxy)acetate.

10. A process for the use of a microemulsion as claimed in claim 1 for preparing aqueous preparations of pesticidal active substances.

11. A microemulsion as claimed in claim 1, comprising 20–35% by weight of active substance; 10–50% by weight of solvent or solvent mixture; 15–25% by weight of emulsifier or wetting agent; 1–10% by weight of cosolvent or antifreeze, and 15–50% by weight of water.

12. A microemulsion comprising 3–50% by weight of at least one herbicidally active substance from the class of the phenoxyphenoxy- and heteroaryloxyphenoxycarboxylic acid derivatives; 5–60% by weight of at least one dispersant from the class of the fatty alcohol polyoxypropylene-polyoxyethylene ethers and of the polyoxypropylene block copolymers; 10–40% by weight of at least one emulsifier or wetting agent from the group consisting of calcium dodecylbenzenesulfonate, fatty acid polyglycol esters of the ethoxylated nonylphenols and of the alkanol polyglycol ethers; 0.1–15% by weight of one or more organic solvents; and 5–70% by weight of water.

13. A microemulsion as claimed in claim 11, further comprising at least one compound selected from the group of the 1-aryl-3alkoxycarbonyl-5alkyl-1,2,4-triazoles, 1aryl-5-alkoxycarbonylpyrazoline-3-carboxylates and 5-substituted 8-quinolinoxy-acetates.

14. A microemulsion as claimed in claim 7, further comprising fenoxaprop-P-ethyl as the active substance in combination with a 1aryl-3-alkoxycarbonyl-5-alkyl-1,2,4-triazole as a safener;
   nonylphenol 10 EO and ($C_{12}$–$C_{18}$) fatty acid polyglycol ester 40 EO as dispersant;
   calcium dodecylbenzene-sulfonate in butanol as emulsifier, in further combination with n-butoxy polyoxypropylene-polyoxyethylene ether, ethoxylated soya oil, glycerol and water.

* * * * *